(12) United States Patent
Suckau

(10) Patent No.: US 12,431,219 B2
(45) Date of Patent: Sep. 30, 2025

(54) METHODS FOR DETERMINING ISOMERIC AMINO ACID RESIDUES OF PROTEINS AND PEPTIDES

(71) Applicant: Bruker Daltonik GmbH, Bremen (DE)

(72) Inventor: Detlev Suckau, Grasberg (DE)

(73) Assignee: Bruker Daltonics GmbH & Co. KG, Bremen (DE)

( * ) Notice: Subject to any disclaimer, the term of this patent is extended or adjusted under 35 U.S.C. 154(b) by 764 days.

(21) Appl. No.: 16/838,386

(22) Filed: Apr. 2, 2020

(65) Prior Publication Data

US 2020/0327961 A1 Oct. 15, 2020

Related U.S. Application Data

(60) Provisional application No. 62/833,864, filed on Apr. 15, 2019.

(51) Int. Cl.
G16B 40/10 (2019.01)
G01N 33/68 (2006.01)

(52) U.S. Cl.
CPC ......... *G16B 40/10* (2019.02); *G01N 33/6848* (2013.01); *G01N 2560/00* (2013.01)

(58) Field of Classification Search
None
See application file for complete search history.

(56) References Cited

U.S. PATENT DOCUMENTS

| 6,639,212 | B1 | 10/2003 | Guevremont et al. |
| 7,838,826 | B1 | 11/2010 | Park |
| 9,683,964 | B2 | 6/2017 | Park |
| 9,891,194 | B2 | 2/2018 | Mann et al. |
| 11,401,305 | B2 | 8/2022 | Binder et al. |
| 2012/0273670 | A1 | 11/2012 | Park et al. |

(Continued)

FOREIGN PATENT DOCUMENTS

| CN | 108519485 A | 9/2020 |
| CN | 106749600 | 11/2020 |

(Continued)

OTHER PUBLICATIONS

Jia, C. et al. Site-Specific Characterization of D-Amino Acid Containing Peptide Epimers by Ion Mobility Spectrometry, Analytical Chemistry, 2014, 86, 2972-2981. (Year: 2013).*

(Continued)

*Primary Examiner* — Xiaoyun R Xu
(74) *Attorney, Agent, or Firm* — Benoît & Côté Inc.

(57) ABSTRACT

The present invention relates to a mass spectrometric method for determining isomeric amino acid residues of a peptide and comprises the steps of: generating a list of peptide candidates using the amino acid lead sequence of the peptide, said lead sequence comprising positions of determined amino acid residues and at least one position with undetermined isomeric amino acid residues; predicting the collision cross section for each peptide candidate; comparing the predicted collision cross section of each peptide candidate with an experimentally determined collision cross section of the peptide and assigning the isomeric amino acid residues of the best matching peptide candidate to the isomeric amino acid residues of the peptide.

23 Claims, 6 Drawing Sheets

(56) References Cited

U.S. PATENT DOCUMENTS

2016/0262224 A1 9/2016 Lee et al.

FOREIGN PATENT DOCUMENTS

CN 109153996 A 3/2022
WO 2014170664 A2 10/2014

OTHER PUBLICATIONS

Baird, M.A. Complete Characterization of Post-Translationally Modified Isomeric Peptides by Linear and Non-Linear Ion Mobility, and Tandem Mass Spectrometry, Thesis for Bachelor of Science, Wichita State University, Wichita, Ks (Year: 2018).*
Shah, A.R. et al. Machine learning based prediction for peptide drift times in ion mobility spectrometry, Bioinformatics, 26(13), 1601-1607 (Year: 2010).*
Meier, Florian et al. "Parallel Accumulation-Serial Fragmentation (PASEF): Multiplying Sequencing Speed and Sensitivity by Synchronized Scans in a Trapped Ion Mobility Device", J. Proteome Res. 2015, 14, pp. 5378-5387.
Armirotti et al., "How to Discriminate Between Leucine and Isoleucine by Low Energy ESI-TRAP MSn," J Am Soc Mass Spectrom, 2007, 18, pp. 57-63.
Srebalus Barnes, C.A. et al., "Resolving Isomeric Peptide Mixtures: a Combined HPLC/Ion Mobility-TOFMS Analysis of a 4000-Component Combinatorial Library", Analytical Chemistry, vol. 74, (2002), pp. 26 to 36.

* cited by examiner

METHODS FOR DETERMINING ISOMERIC AMINO ACID RESIDUES OF PROTEINS AND PEPTIDES

BACKGROUND OF THE INVENTION

Field of the Invention

The methods according to the present invention relate to the differentiation of peptides and proteins comprising isomeric amino acid residues by mass spectrometry.

Description of the Related Art

An article by Hurtado et al. (Mass Spec. rev., 2012, 31, 609-625: "Differentiation of isomeric amino acid residues in proteins and peptides using mass spectrometry") reviews developments in mass spectrometry methodologies in the identification of structural and spatial isomers in biological macromolecules, such as aspartic acid and iso-aspartic acid (Asp/IsoAsp), leucine and isoleucine (Leu/Ile), glutamic acid and g-glutamic acid, and D/L enantiomers.

Hurtado et al. teach that characterization and differentiation of isomers in biological macromolecules using mass spectrometry is one of the most significant challenges facing scientists in the field. The capability of high-resolution MS instruments along with the development of new fragmentation methods provides the ability to indirectly differentiate between isomers. This ability has enabled mass spectrometry to evolve into a multidisciplinary technique incorporating areas such as pharmaceutical research, proteomics, polymer science, and medicine.

Hurtado et al. further teach that many attempts have been made to distinguish isomeric forms in peptides, for example (a) ionization/fragmentation by fast atom bombardment (FAB); (b) collisionally activated dissociation at high collision energies (HE-CAD, also termed HE-CID) in the 500 eV range; (c) fragmentation by electron capture dissociation ECD, in particular by with increased electron energies (hot ECD or HE-ECD); and (d) fragmentation by electron transfer dissociation (ETD).

An article by Armirotti et al. (Am Soc Mass Spectrom 2007, 18, 57-63: "How to Discriminate Between Leucine and Isoleucine by Low Energy ESI-TRAP MS$^n$") teaches that, in peptide sequencing experiments involving a single step tandem mass acquisition, leucine and isoleucine are indistinguishable and proposes a mass spectrometric method to distinguish between these two amino acids in consecutive MS$^n$ experiments, exploiting a gas-phase fragmentation of isoleucine that leads to a diagnostic 69 Da ion.

SUMMARY OF THE INVENTION

In a first aspect, the present invention provides a method for determining isomeric amino acid residues of a peptide. The method comprises the steps: acquiring a fragment mass spectrum of the peptide (MS$^2$); determining a lead sequence of the peptide using the fragment mass spectrum, said lead sequence comprising positions of determined amino acid residues and at least one position with undetermined isomeric amino acid residues; experimentally determining the ion mobility or collision cross section of the peptide in the gas phase; generating a list of peptide candidates which have different isomeric amino acid residues at at least one position and comparing a predetermined or predicted ion mobility or collision cross section of the peptide candidates with the experimentally determined ion mobility or collision cross section of the peptide and assigning the isomeric amino acid residues of the best matching peptide candidate to the isomeric amino acid residues of the peptide.

The lead sequence of the peptide can for example be determined by matching the fragment mass spectrum of the peptide with fragment mass spectra of peptides stored in a library for which the lead sequence is known. The peptide is preferably fragmented by low energy collision induced dissociation (CID) (in particular with collision energy below 100 eV), but can also be fragmented by other fragmentation methods such as surface induced dissociation (SID) or ultraviolet photo-dissociation (UVPD). Low energy means that substantially no inner bonds inside an amino acid residue are cleaved, but rather bonds between amino acid residues are broken (back bone cleavages). In addition, the mass of the peptide can be experimentally determined from the fragment mass spectrum or from a mass spectrum of the peptide and used to determine the lead sequence of the peptide.

In a first embodiment of multiple peptides, a fragment mass spectrum for a single peptide is acquired in a data dependent acquisition mode by separating the multiple peptides in time according to ion mobility, and additionally isolating the single peptide according to mass and fragmenting the single peptide in a fragmentation cell. The multiple peptides can be separated in time according to ion mobility before or after filtering according to mass. Prior to the acquisition of the fragment mass spectrum of the peptide, the multiple peptides are preferably separated in time according to ion mobility and mass spectra of the separated peptides are acquired in order to obtain an ion mobility/mass map of the multiple peptides.

In a second embodiment of multiple peptides, the multiple peptides are separated in time according to ion mobility, and mass spectra of the separated peptides are acquired in order to obtain an ion mobility/mass map of the multiple peptides and the temporal profiles of the multiple peptides. Multiple fragment spectra are acquired in a data independent acquisition mode by separating the multiple peptides in time according to ion mobility, fragmenting the separated peptides without mass isolating a single peptide and assigning those fragment mass signals to the fragment mass spectrum of a specific peptide which has a correlated temporal profile.

In a second aspect, the present invention provides a method that differs from the method of the first aspect in that the lead sequence of the peptide is known and provided, i.e. that the lead sequence of the peptide is not determined using a fragment mass spectrum which is acquired as part of the method. The method comprises the steps: providing a known lead sequence of the peptide, said lead sequence comprising positions of determined amino acid residues and at least one position with undetermined isomeric amino acid residues; experimentally determining the ion mobility or collision cross section of the peptide in the gas phase; generating a list of peptide candidates which have different isomeric amino acid residues at the at least one position; comparing predetermined or predicted ion mobility or collision cross section of the peptide candidates with the experimentally determined ion mobility or collision cross section of the peptide and assigning the isomeric amino acid residues of the best matching peptide candidate to the isomeric amino acid residues of the peptide.

In both aspects, the lead sequence relates to the primary structure of the peptide and comprises positions of determined amino acid residues and at least one position with undetermined isomeric amino acid residues. The lead sequence preferably covers more than 75%, more preferably 90%, most preferably 100% of the determined amino acid residues.

The peptide is a polypeptide with more than 5 and less than 50 amino acids residues, in particular with more than 7 and less than 30 amino acids residues. The peptide can for example be a fragment of a protein with a region of biological specificity, in particular an antibody, more particular a monoclonal antibody, or a fragment of a construct that comprises an antibody or fragments of it. The peptide is preferably a fragment derived from the complementarity-determining region (CDR) of an antibody. The peptide can also be a peptide-aptamer or a fragment of a peptide-aptamer. Peptide-aptamers are artificial proteins selected or engineered to bind specific target molecules and comprise one or more peptide loops of variable sequence displayed by a protein scaffold. Peptide-aptamers are typically isolated from combinatorial libraries and often subsequently improved by directed mutation of variable regions and selection. The terms "peptide" and "peptide ion" as well as "protein" and "protein ion" are used interchangeably for ease of comprehension.

The isomeric amino acid residues have the same mass and refer for example to one of leucine/isoleucine, cis-proline/trans-proline, aspartic acid/iso-aspartic acid, α-/γ-glutamic acid and enantiomeric amino acid residues (left-handed and right-handed amino acid residues, L/D-amino acid residues). The number of isomeric amino acid residues in the peptide is preferably less than 5, more preferably less than 3. The number of peptide candidates is limited to $2^N$, with N being the number of positions with isomeric amino acid residues.

In order to differentiate enantiomeric amino acid residues, it might be necessary to use an enantiomeric gas phase environment for experimentally separating the peptides in the gas phase according to ion mobility, for example by providing an enantiomeric component to the gas phase or by inducing a gas phase reaction to differentiate the collision cross section of the peptides with different enantiomeric amino acid residues. Differentiation and modifications in the liquid phase are also possible.

The determination of isomeric amino acid residues of a peptide can be part of the quality control during or after the production of a protein, in particular of a monoclonal antibody, antibody-drug-conjugates, therapeutic proteins, vaccines, and other protein-based biopharmaceuticals. One of the barriers to the commercialization of monoclonal antibodies is the risk of degradation via deamidation and the isomerization of aspartic acid to iso-aspartic acid in the complementarity-determining regions of the light chains and heavy chains. The protein can be produced by a synthetic expression system or a cell-based expression system. The cell-based expression system can for example be based on bacterial cells, yeast cells, insect cells or mammalian cells, for example Chinese Hamster ovary (CHO) or Human embryonic kidney (HEK) cells.

The peptide can be generated by enzymatically digesting a protein in solution, e.g. by a tryptic digest. The peptide is then preferably separated from other digest peptides of the protein by chromatography or electrophoresis prior to acquiring the fragment ion mass spectrum of the peptide.

The peptide can also be generated by fragmenting an intact protein in the gas phase, for example by surface induced dissociation (SID) or ultraviolet photo-dissociation (UVPD). In case of a protein mixture, the intact protein can be separated from other proteins of the mixture in the liquid phase by liquid chromatography or electrophoresis prior to the transfer into the gas phase, or it can be separated from other proteins of the mixture in the gas phase by ion mobility.

The methods according to the present invention are preferably performed on a hybrid mass spectrometric system comprising an ion source, at least one mobility separator, a mass filter, a fragmentation cell and a mass analyzer. The ion source can comprise means for electrospray ionization at atmospheric pressure or sub-ambient pressure, matrix-assisted laser desorption/ionization, or chemical ionization. The ion mobility or collision cross section of the peptide in the gas phase is experimentally determined by using an ion mobility separator or ion mobility spectrometer, in particular one of a drift type ion mobility separator/spectrometer, travelling wave ion mobility separator/spectrometer, trapped ion mobility separator/spectrometer (TIMS), differential mobility separator/spectrometer (DMS) and field asymmetric ion mobility separator/spectrometer (FAIMS). The mass analyzer can be one of a quadrupole mass filter, a time-of-flight mass analyzer, a time-of-flight mass analyzer with orthogonal ion injection, a RF ion trap, an electrostatic ion trap (like an orbitrap or cassini-trap) and an ion-cyclotron-resonance trap.

The ion mobility or collision cross section of the peptide in the gas phase can be experimentally determined a second time at an increased resolution. In particular, a TIMS separator can be operated in a so-called temporal zoom mode with an increased resolution in a limited region of interest as described in laid-open publication US 2012/0273670 A1. The mobility resolution in the region of interest can be higher than 100, in particular higher than 200, while the overall scan time of the TIMS separator is less than 200 ms, in particular less than 100 ms.

The ion mobility or collision cross section of the candidate peptides is preferably predicted by a supervised machine learning algorithm, in particular by an artificial neural network or support vector regression. The artificial neural network can for example be a bidirectional long-short-term-memory (LSTM) network or a convolutional deep neural network (CNN). A supervised machine learning algorithm is trained on a large data set of training peptides for which the ion mobility or collisional cross section are known and for which the amino acid sequences are at least substantially known. The data set comprises a subset of training peptides with determined isomeric amino acid residues wherein the subset is preferably more than 10% of the whole data set, more preferably more than 20%, most preferably more than 50%. The number of training peptides is preferably greater than 1000, more preferably greater than 5000, most preferably greater than 10,000. The training peptides can for example be simply represented by their amino acid sequence in which substantially all amino acid residues are determined.

The methods according to the invention have the advantage that they fit to bottom-up as well as top-down work flows in the field of proteomics in which commonly low energy CID is used for fragmentation. They do not need high energies to break specific bonds inside isomeric amino acid residues and are therefore not limited to isomeric amino acid residues with specific fragmentation pattern, but can generally be applied to isomeric amino acid residues. Furthermore, they neither need time-consuming fragmentation techniques, like ECD and ETD, nor higher order fragment mass spectra ($MS^n$, n≥3) nor expensive mass analyzers with high mass resolution (R>100,000). It is surprising that peptides having the same amino acid sequence except for isomeric amino acid residues can be separated according to their ion mobility and that the isomeric amino acid residues can be determined without measuring the ion mobilities or collision cross sections for all peptide candidates having different isomeric amino acid residues.

DETAILED DESCRIPTION

While the invention is shown and described with reference to a number of different embodiments thereof, it will be recognized by those skilled in the art that various changes in form and detail may be made herein without departing from the scope of the invention as defined by the claims.

Figure 1:
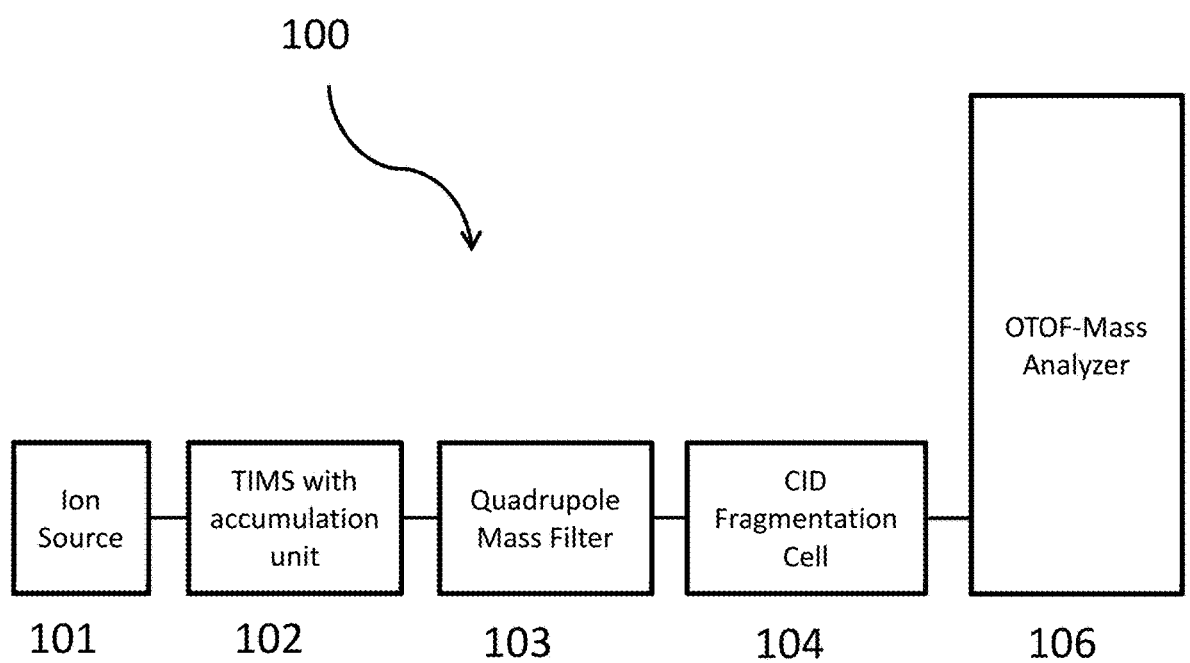
FIG. 1 shows a schematic representation of a hybrid mass spectrometric system (100) known from prior art for bottom-up proteomics which comprises an ion source (101), a TIMS separator (102), a quadrupole mass filter (103), a CID fragmentation cell (104) and a time-of-flight mass analyzer with orthogonal injection (106).

FIG. 1 shows a schematic diagram of a hybrid mass spectrometric system (100) known from prior art which comprises an ion source (101), an TIMS separator (102), a quadrupole mass filter (103), a CID fragmentation cell (104) and a time-of-flight mass analyzer with orthogonal injection (OTOF-mass analyzer (106)). Optionally, a liquid phase substance separator, e.g. liquid chromatograph, is coupled to the ion source (101).

U.S. Pat. No. 7,838,826 B1 discloses a compact ion mobility separator which is termed "trapped ion mobility spectrometer" (TIMS). The length of the essential mobility separation unit amounts to about five centimeters only. A gas flow in the separation unit drives ions against a counter-acting electric DC field barrier at which the ions get axially trapped and separated in space according to ion mobility during an accumulation phase. The ions are radially confined by a quadrupolar RF field. In a scan phase, the trapped ions are subsequently eluted from the electric DC field barrier in time by decreasing the height of axial electric DC field. Ions are successively released from low ion mobility to higher ion mobility. Mass spectra of the temporally separated ions can be acquired by a downstream mass analyzer resulting in so called IMS/MS maps.

U.S. Pat. No. 9,683,964 B2 discloses a TIMS separator with an accumulation unit located upstream of the separation unit for storing ions during the scan phase.

U.S. Pat. No. 9,891,194 B2 discloses a multi-cycle method to acquire fragment ion spectra of substances in complex mixtures using hybrid mass spectrometric system (100). In a first measurement cycle, an IMS/MS map is acquired from which several ion species with distinct masses and distinct mobility scan times are selected. In second measurement cycles, ions are again separated in time according to ion mobility and the mass filter (103) is adjusted during the mobility separation to transmit only the selected ion species. The transmitted ion species are fragmented by collision induced dissociation in the fragmentation cell (104) and then fragment mass spectra are acquired for each one of the selected ion species by OTOF mass analyzer (106).

Figure 2:
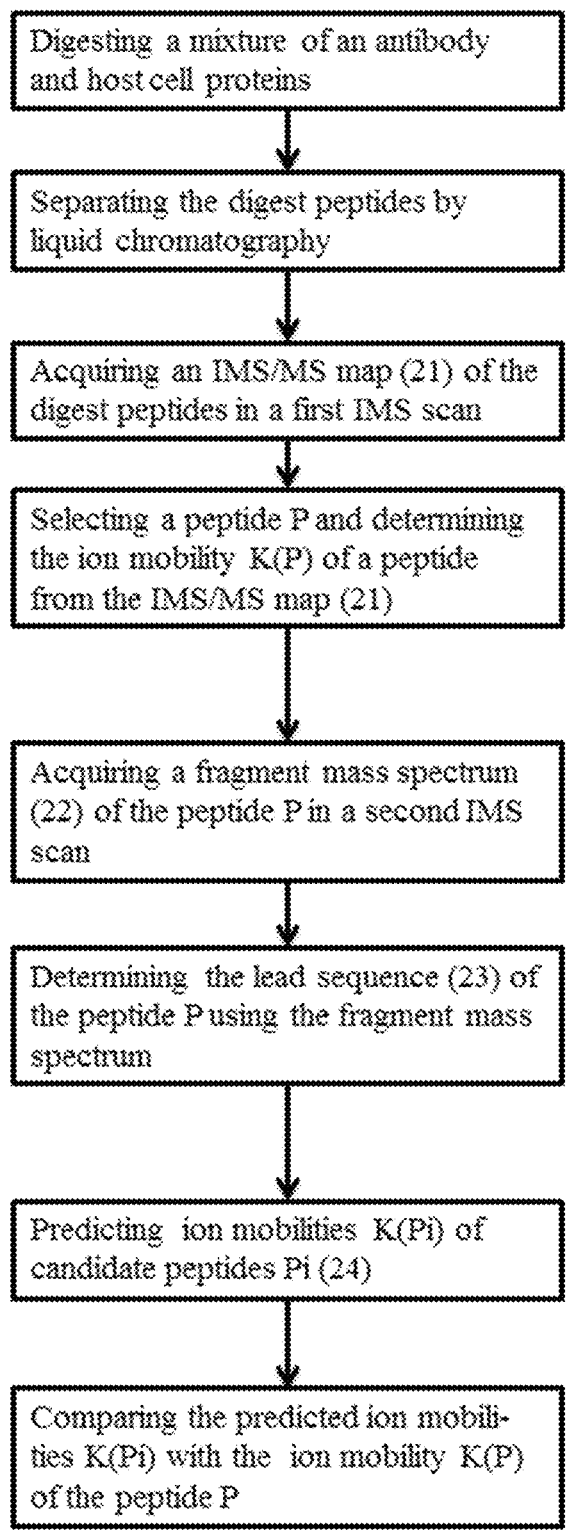
FIG. 2 shows a flow chart of a first exemplary method according to the present invention for analyzing a mixture of an antibody and host cell proteins.
Figure 2:
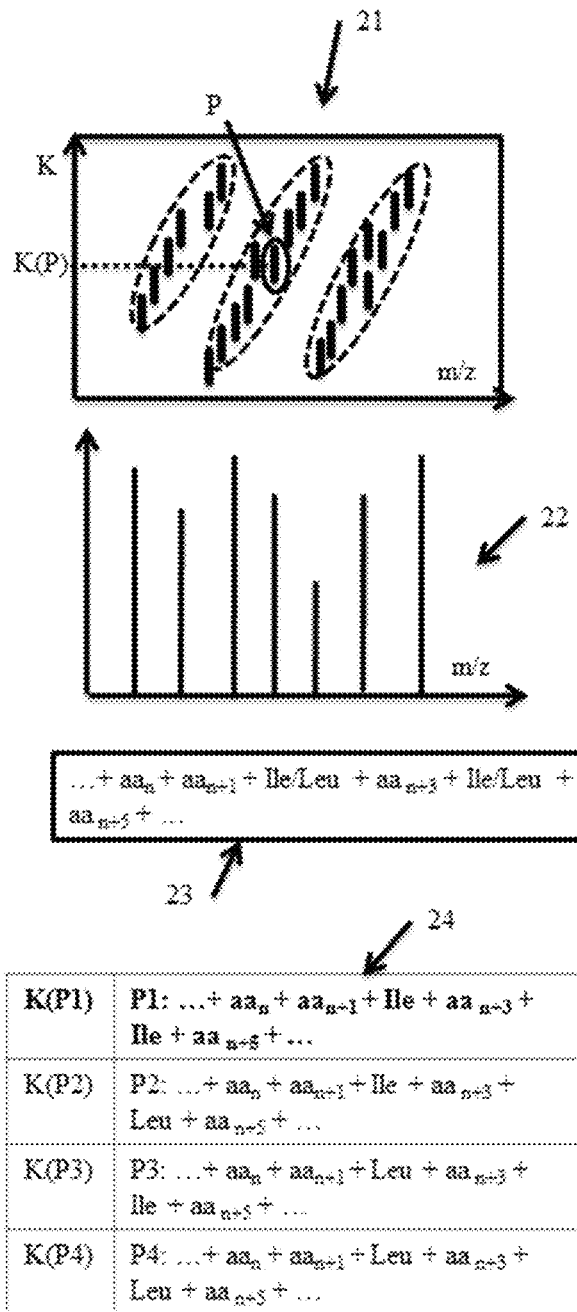

FIG. 2 shows a flow chart of a first exemplary method according to the present invention for analyzing a mixture of an antibody and host cell proteins using the hybrid mass spectrometric system (100).

Host cell proteins (HCPs) are process-related impurities, expressed by the host cell used for production of proteins. During a purification process, the majority of the HCPs are removed, but HCPs remain to a certain amount in the distributed products, which can be monoclonal antibodies (mAbs), antibody-drug-conjugates (ADCs), therapeutic proteins, vaccines, and other protein-based biopharmaceuticals.

The antibody and host cell proteins are enzymatically digested in the liquid phase by using trypsin. The digest peptides are separated by a liquid chromatograph (not shown in FIG. 1) which is coupled to an electrospray ion source (101).

In a first IMS scan, an IMS/MS map (21) of the digest peptides is acquired by the OTOF-mass analyzer (106) while the mass filter (103) and the CID fragmentation cell (104) are operated as transmitting ion guides. The IMS/MS map (21) shows three distinct subsets (marked dotted) which correspond to different charge states of the digest peptides with increasing charge state from left to right. A peptide P is selected and the ion mobility K(P) of a peptide is experimentally determined from the IMS/MS map (21).

In a second IMS scan, the peptide P is isolated in a data-dependent mode from the other digest peptides by linking the TIMS separator (102) and the mass filter (103). The isolated peptide P is transferred to the CID fragmentation cell (104) and fragmented by low energy CID. The fragment mass spectrum (22) of the isolated peptide P is acquired by the OTOF-mass analyzer (106).

The peptide P is identified by comparing the acquired fragment mass spectrum of the peptide P with fragment mass spectra of known peptides stored in a library, in particular by additionally using the mass of the peptide P which is preferably determined from the IMS/MS map (21).

The lead sequence (23) of the identified peptide P comprises two undetermined isomeric leucine/isoleucine residues. These two isomeric amino acid residues result in a list (24) of four peptide candidates P1 to P4 for which ion mobilities K(P1) to K(P4) are predicted using a support vector regression. The isomeric amino acid residues of the candidate peptide P1 are assigned to the peptide P due to the best match between the predicted ion mobility K(P1) and the experimentally determined ion mobility of the peptide K(P).

Figure 3:
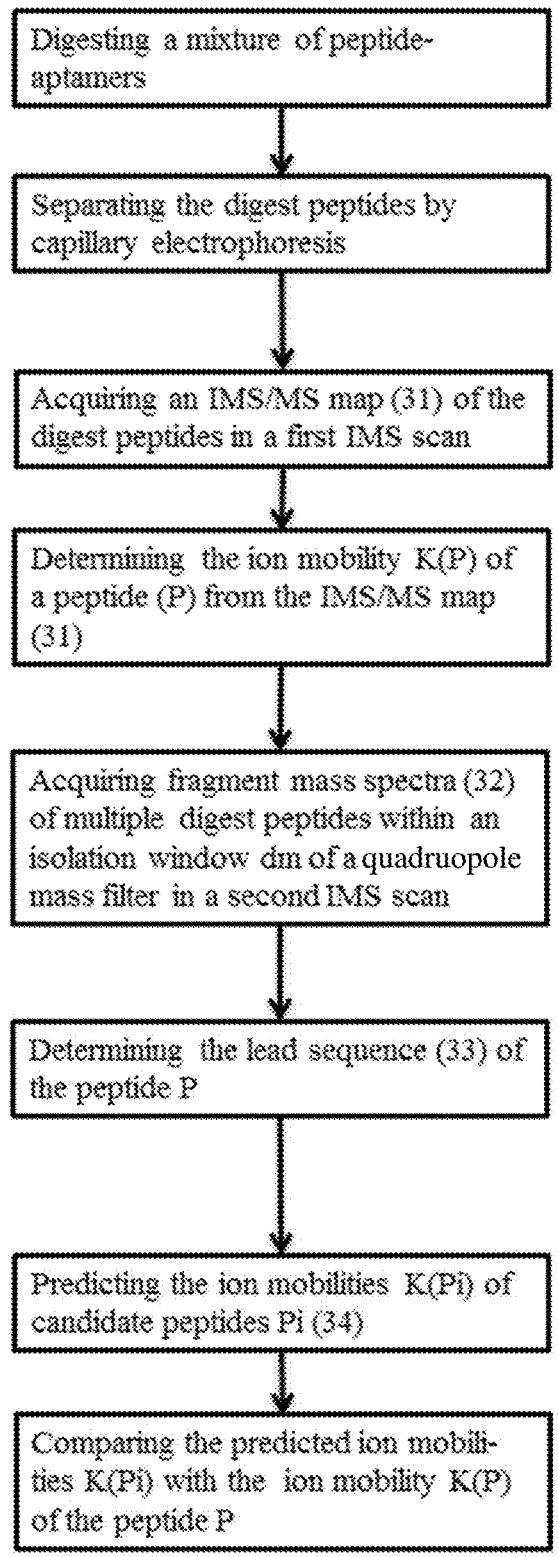
FIG. 3 shows a flow chart of a second exemplary method according to the present invention for analyzing a mixture of peptide-aptamers.
Figure 3:
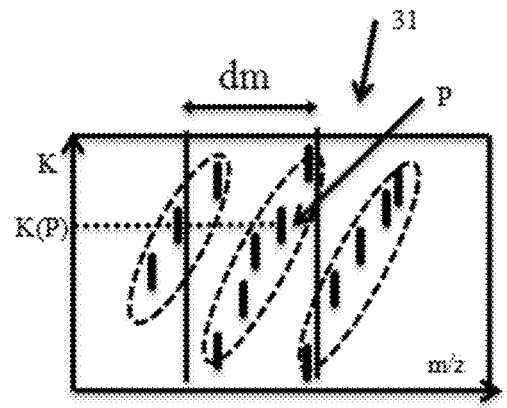
Figure 3:
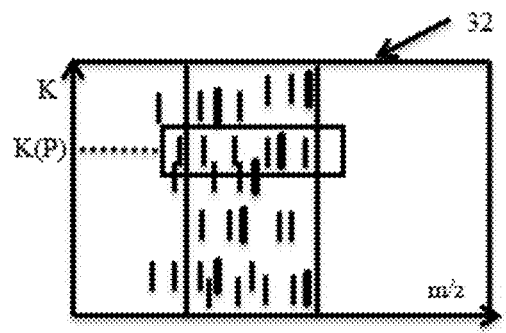

FIG. 3 shows a flow chart of a first exemplary method according to the present invention for analyzing a mixture of peptide-aptamers using the hybrid mass spectrometric system (100).

The peptide-aptamers of the mixture are enzymatically digested in the liquid phase by using trypsin. The digest peptides are separated by an electrophoretic device (not shown in FIG. 1) which is coupled to an electrospray ion source (101).

In a first IMS scan, an IMS/MS map (31) of the digest peptides is acquired by the OTOF-mass analyzer (106) while the mass filter (103) and the CID fragmentation cell (104) are operated as transmitting ion guides. The IMS/MS map (31) shows three distinct subsets (marked dotted) which correspond to different charge states of the digest peptides with increasing charge state from left to right. A peptide P is selected and the temporal ion mobility profile of the peptide P is experimentally determined from the IMS/MS map (31).

In a second IMS scan, the mass filter (103) is set to transmit multiple digest peptides within a mass window dm such that multiple fragment mass spectra (32) of multiple digest peptides are acquired during the second IMS scan which can overlap in time. All fragment mass signals whose temporal ion mobility profile correlates with the temporal ion mobility profile of the peptide P are assigned to the fragment mass spectrum of the peptide P (data-independent analysis, DIA). The lead sequence (33) of the peptide P is determined using the fragment mass spectrum of the peptide P by identifying the peptide in a library search as described in the first exemplary method.

The lead sequence (33) of the identified peptide P comprises one undetermined isomeric aspartic/iso-aspartic residue which results in a list (34) of two peptide candidates P1 to P2 for which ion mobilities K(P1) to K(P2) are predicted using a deep neural network. The isomeric amino acid residue of the candidate peptide P1 is assigned to the peptide P due to the best match between the predicted ion mobility K(P1) and the experimentally determined ion mobility of the peptide K(P).

Figure 4:
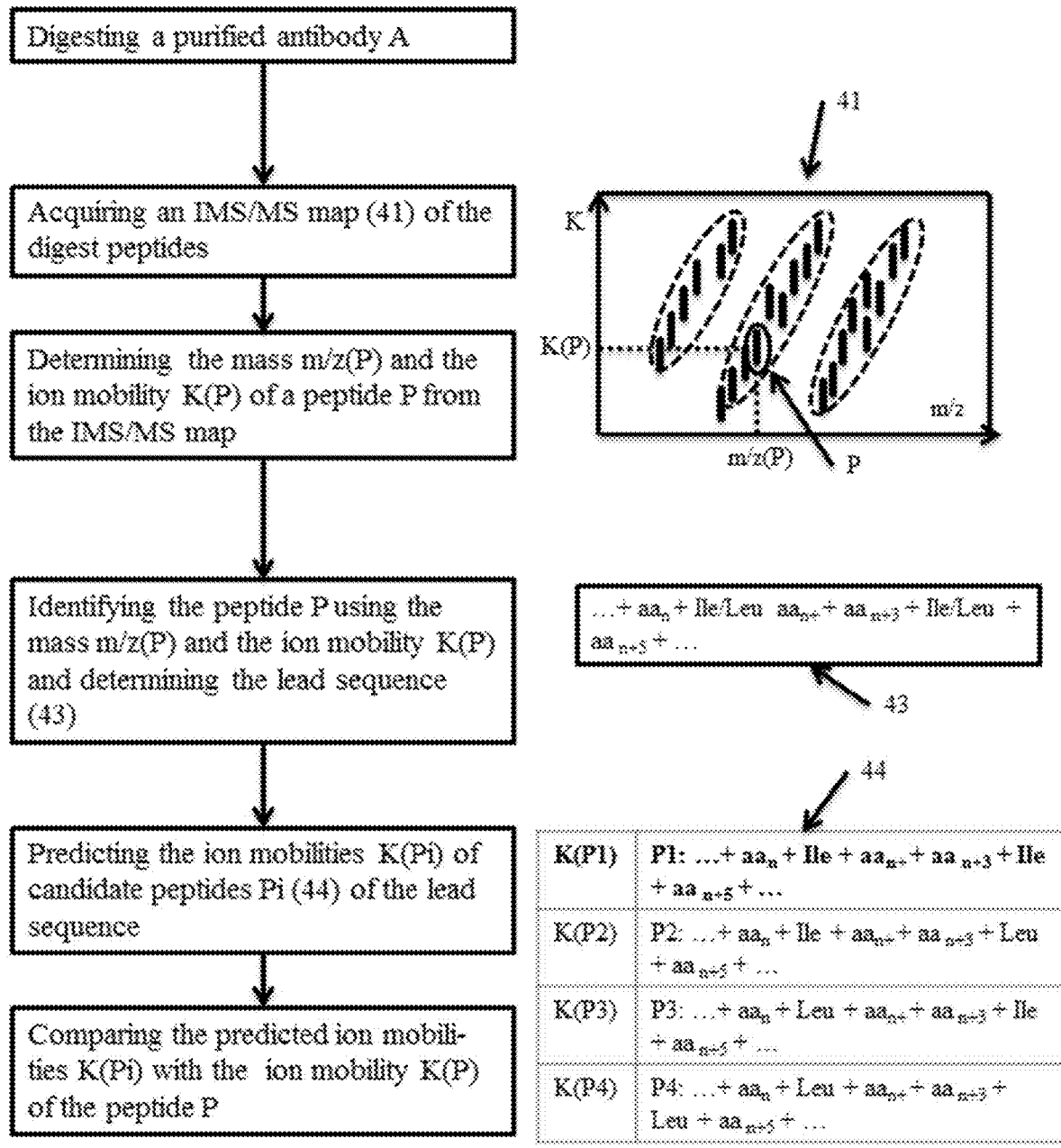
FIG. 4 shows a flow chart of a third exemplary method according to the present invention for analyzing a purified antibody.

FIG. 4 shows a flow chart of a third exemplary method according to the present invention for analyzing a purified antibody A using the hybrid mass spectrometric system (100).

The purified antibody A is enzymatically digested in the liquid phase by using trypsin.

An IMS/MS map (41) of the digest peptides is acquired by the OTOF-mass analyzer (106) while the mass filter (103) and the CID fragmentation cell (104) are operated as transmitting ion guides. The IMS/MS map (41) shows three distinct subsets (marked dotted) which correspond to different charge states of the digest peptides with increasing charge state from left to right. A peptide P is selected in the IMS/MS map (41) and the mass m/z(P) and the ion mobility K(P) of the peptide P is experimentally determined from the IMS/MS map (41).

The peptide P is identified by comparing the mass m/z(P) and the ion mobility K(P) with pre-determined masses and ion mobilities of known digest peptides of the antibody and the lead sequence (43) of the peptide P is determined. Optionally, a second IMS/MS map can be acquired in an additional IMS scan wherein the mobility resolution around the ion mobility K(P) is increased such that peptide variants with different isomeric amino acid residues can be differentiated or further differentiated in the second IMS/MS map.

The lead sequence (43) of the identified peptide P comprises two undetermined isomeric leucine/isoleucine residues. These two isomeric amino acid residues result in a list (44) of four peptide candidates P1 to P4 for which ion mobilities K(P1) to K(P4) are predicted using a long-short-term-memory (LSTM) network. The isomeric amino acid residues of the candidate peptide P1 are assigned to the peptide P due to the best match between the predicted ion mobility K(P1) and the experimentally determined ion mobility of the peptide K(P).

Figure 5:
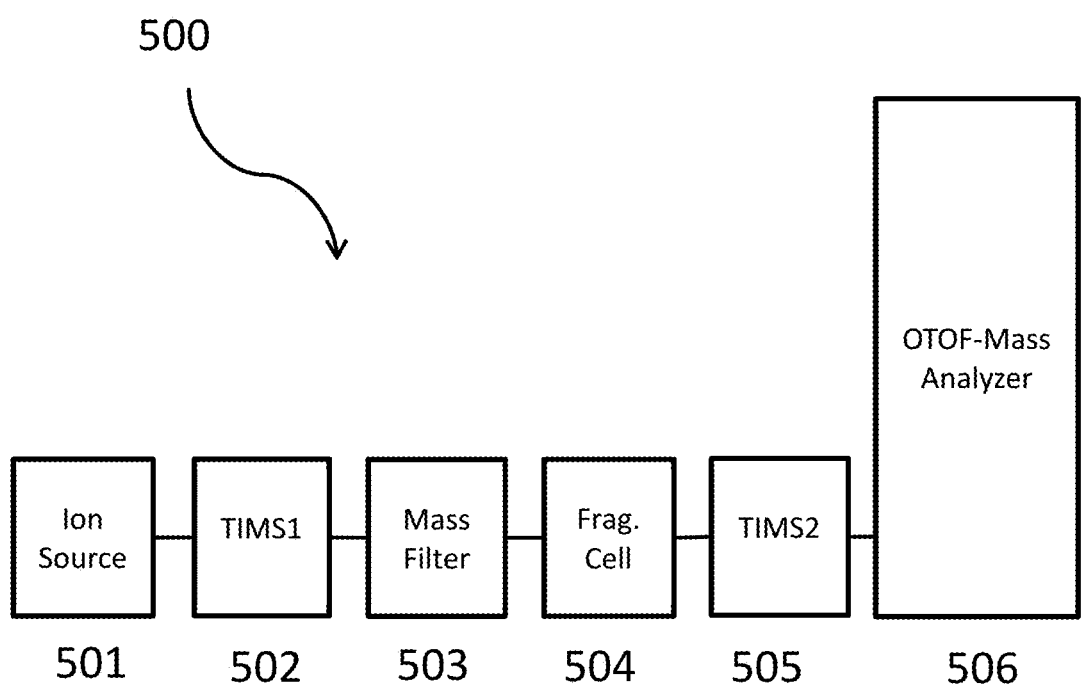
FIG. 5 shows a schematic representation of a hybrid mass spectrometric system (500) known from prior art which comprises an ion source (501), a first TIMS separator with parallel accumulation (502), a mass filter (503), a fragmentation cell (504), a second TIMS separator with parallel accumulation (505) and a time-of-flight mass analyzer with orthogonal injection (506).

FIG. 5 shows a schematic diagram of a hybrid mass spectrometric system (500) known from U.S. patent application Ser. No. 16/262,224 which comprises an ion source (501), a first TIMS separator with parallel accumulation (502), a mass filter (503), a fragmentation cell (504), a second TIMS separator with parallel accumulation (505) and a time-of-flight mass analyzer with orthogonal injection (OTOF-mass analyzer) (506).

The mass spectrometric system (500) enables isolating an intact protein from a mixture by linking the first TIMS separator (502) and the mass filter (503) and fragmenting the isolated protein in the gas phase into fragment peptides which are further analyzed by the downstream second TIMS separator (505) and the time-of-flight mass analyzer (506). Optionally, a liquid phase substance separator, e.g. liquid chromatograph or capillary electrophoresis device, can be coupled to the ion source (501) and a combined mass filter/fragmentation cell can be located between the second TIMS separator (505) and the OTOF-mass analyzer (506).

The fragmentation cell (504) can comprise means for collision induced dissociation (CID), surface induced dissociation (SID), photo-dissociation (PD), infrared multiple photo-dissociation (IRMPD), ultraviolet photo-dissociation (UVPD), electron capture dissociation (ECD), electron transfer dissociation (ETD), collisional activation after electron transfer dissociation (EThcD), activation concurrent with electron transfer dissociation (AI-ETD) or fragmentation by reactions with highly excited or radical neutrals.

Figure 6:
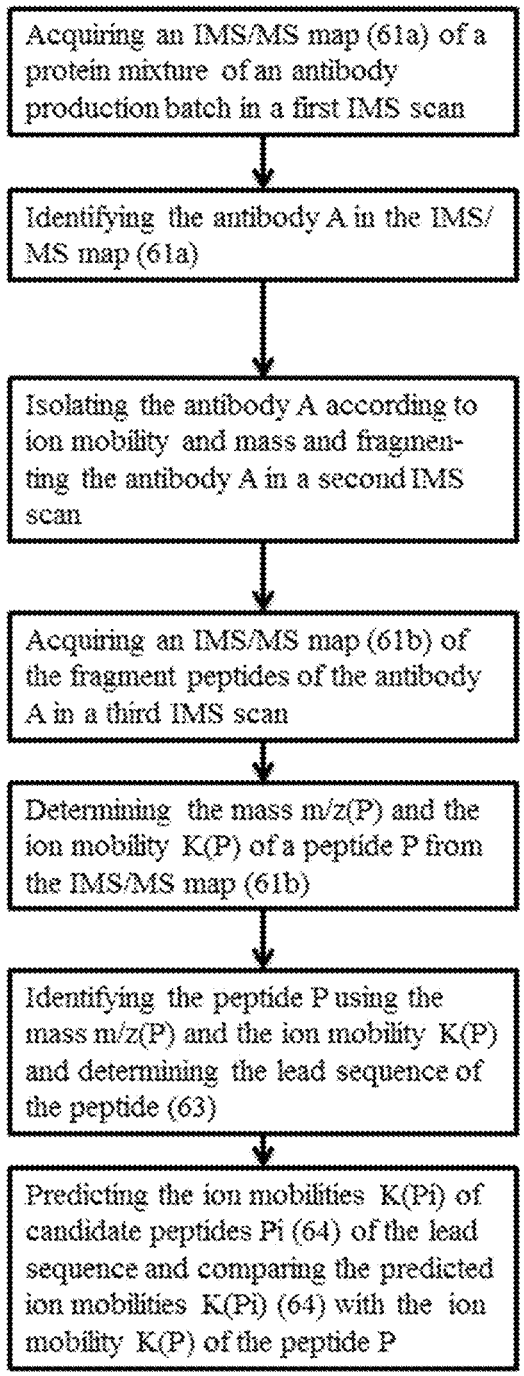
FIG. 6 shows a flow chart of a fourth exemplary method according to the present invention for analyzing a protein mixture of an antibody production batch.
Figure 6:
Figure 6:
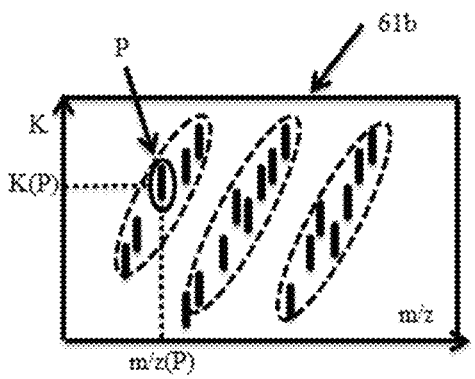

FIG. 6 shows a flow chart of a fourth exemplary method according to the present invention for analyzing a protein mixture of an antibody production batch using the hybrid mass spectrometric system (500). As described in the first exemplary method, the mixture can comprise host cell proteins.

In a first IMS scan of the TIMS separator (502), an IMS/MS map (61a) of the protein mixture is acquired by the OTOF-mass analyzer (506) while the mass filter (503), the fragmentation cell (504) and the second TIMS separator (505) are operated as transmitting ion guides. The antibody A is identified in the IMS/MS map (61a) using the mass m/z(A) and ion mobility K(A).

In a second IMS scan of the first TIMS separator (502), the antibody A is isolated from the mixture of proteins by linking the first TIMS separator (502) and the mass filter (503). The isolated antibody A is transferred to the fragmentation cell (504) and fragmented into fragment peptides, preferably by surface induced dissociation (SID) or ultraviolet photo-dissociation (UVPD).

In a first IMS scan of the second TIMS separator (505), an IMS/MS map (61b) of the fragment peptides is acquired by the OTOF-mass analyzer (506). The mass and the ion mobility of a peptide P are experimentally determined in the IMS/MS map (61b). The peptide P is identified by the mass m/z(P) and the ion mobility K(P). The lead sequence (63) of the identified peptide P is determined and comprises two undetermined isomeric leucine/isoleucine residues. The two isomeric amino acid residues result in a list (64) of four peptide candidates P1 to P4 for which ion mobilities K(P1) to K(P4) are predicted using a convolutional deep neural network (CNN). The isomeric amino acid residues of the candidate peptide P1 are assigned to the peptide P due to the best match between the predicted ion mobility K(P1) and the experimentally determined ion mobility of the peptide K(P).

The invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A method for determining isomeric amino acid residues of a peptide of interest, comprising the steps of:
fragmenting the peptide of interest to create fragment ions and acquiring a fragment mass spectrum of the fragment ions;
determining a lead sequence of the peptide of interest using the fragment mass spectrum, said lead sequence comprising positions of determined amino acid residues and at least one position with an undetermined isomeric amino acid residue; and
experimentally determining the ion mobility or collision cross section of the peptide of interest in the gas phase;
generating a list of peptide candidates each having a different isomeric amino acid residue at the at least one position; and
comparing pre-determined or predicted ion mobility or collision cross section of the peptide candidates with the experimentally determined ion mobility or collision cross section of the peptide of interest and assigning the isomeric amino acid residue from the at least one position of the best matching peptide candidate to the at least one position of the undetermined isomeric amino acid residue of the peptide of interest.

2. The method according to claim 1, wherein the isomeric amino acid residues relate to one of leucine/isoleucine, cis-proline/trans-proline, aspartic acid/iso-aspartic acid, α-/γ-glutamic acid and enantiomeric amino acid residues.

3. The method according to claim 1, wherein experimentally determining the ion mobility or collision cross section of the peptide of interest in the gas phase includes using an ion mobility separator or ion mobility spectrometer, in particular one of a drift type ion mobility separator/spectrometer, travelling wave ion mobility separator/spectrometer, trapped ion mobility separator/spectrometer (TIMS), differential mobility separator/spectrometer (DMS) and field asymmetric ion mobility separator/spectrometer (FAIMS).

4. The method according to claim 1, wherein the ion mobility or collision cross section of the peptide candidates is predicted by a supervised machine learning algorithm, an artificial neural network or support vector regression.

5. The method according to claim 1, wherein the mass of the peptide of interest is experimentally determined from the fragment mass spectrum or from an additionally acquired mass spectrum of the peptide of interest and used to determine the lead sequence of the peptide of interest.

6. The method according to claim 1, wherein the peptide of interest is generated by enzymatically digesting a protein in solution, in particular by a tryptic digest.

7. The method according to claim 6, wherein the protein is an antibody, a monoclonal antibody, or a construct that comprises an antibody or fragments of it.

8. The method according to claim 7, wherein the determination of isomeric amino acid residues of a peptide of interest is part of the quality control of the production of the protein.

9. The method according to claim 6, wherein the peptide of interest is separated from other digest peptides of the protein by chromatography or electrophoresis prior to acquiring the fragment ion mass spectrum.

10. The method according to claim 1, wherein the peptide of interest is generated by fragmenting a protein in the gas phase.

11. The method according to claim 10, wherein the protein is separated from other proteins in the liquid phase by chromatography or electrophoresis prior to the transfer into the gas phase and fragmentation.

12. The method according to claim 10, wherein the protein is separated from other proteins in the gas phase by ion mobility prior to fragmentation.

13. The method according to claim 10, wherein the protein is an antibody, a monoclonal antibody, or a construct that comprises an antibody or fragments of it.

14. The method according to claim 13, wherein the determination of isomeric amino acid residues of a peptide of interest is part of the quality control of the production of the protein.

15. The method according to claim 1, wherein the lead sequence of the peptide of interest is determined by matching the fragment mass spectrum with fragment mass spectra of library peptides for which the lead sequence is known.

16. The method according to claim 15, wherein the peptide of interest is fragmented by using one of collision induced dissociation (CID), surface induced dissociation (SID), and infrared multiphoton dissociation (IRMPD).

17. The method according to claim 1, wherein multiple peptides of interest to be analyzed are simultaneously present and a fragment mass spectrum for fragment ions of at least one peptide of interest is acquired in a data dependent acquisition mode by filtering a single peptide as precursor ion according to mass and fragmenting the filtered precursor ion in a fragmentation cell.

18. The method according to claim 17, wherein the multiple peptides of interest are separated in time according to ion mobility before or after filtering according to mass.

19. The method according to claim 18, wherein, prior to the acquisition of the fragment mass spectrum of the fragment ions of the peptide of interest, the multiple peptides of interest are separated in time according to ion mobility and mass spectra of the separated peptides of interest are acquired in order to obtain an ion mobility/mass map of the multiple peptides of interest.

20. The method according to claim 1, wherein multiple peptides of interest to be analyzed are simultaneously present and multiple fragment spectra are acquired in a data independent acquisition mode by separating the multiple peptides of interest in time according to ion mobility, fragmenting the separated peptides of interest without filtering a single peptide of interest according to mass and assigning these fragment mass signals to a fragment mass spectrum of a specific peptide of interest which has a correlated temporal profile.

21. The method according to claim 20, wherein, prior to the acquisition of the multiple fragment mass spectra, the multiple peptides of interest are separated in time according to ion mobility and mass spectra of the separated peptides of interest are acquired in order to obtain an ion mobility/mass map of the multiple peptides of interest.

22. The method according to claim 1, wherein the ion mobility or collision cross section of the peptide of interest in the gas phase is experimentally determined a second time with an increased resolution according to ion mobility or collision cross section, respectively.

23. A method for determining the isomeric amino acid residues of a peptide of interest, comprising the steps of:
providing a known lead sequence of the peptide of interest, said lead sequence comprising positions of determined amino acid residues and at least one position with an undetermined isomeric amino acid residue;
experimentally determining the ion mobility or collision cross section of the peptide of interest in the gas phase;
generating a list of peptide candidates, each having a different isomeric amino acid residue at the at least one position; and
comparing pre-determined or predicted ion mobility or collision cross section of the peptide candidates with the experimentally determined ion mobility or collision cross section of the peptide of interest and assigning the isomeric amino acid residue from the at least one position of the best matching peptide candidate to the at least one position of the undetermined isomeric amino acid residue of the peptide of interest.

\* \* \* \* \*